United States Patent [19]

Guglietta

[11] Patent Number: 6,028,095
[45] Date of Patent: Feb. 22, 2000

[54] TREATMENT OF INFLAMMATORY BOWEL DISEASE USING HISTAMINE $H_3$-RECEPTOR AGONISTS

[75] Inventor: Antonio Guglietta, Ann Arbor, Mich.

[73] Assignee: Warner-Lambert Company, Morris Plains, N.J.

[21] Appl. No.: 09/416,158

[22] Filed: Oct. 11, 1999

Related U.S. Application Data

[60] Provisional application No. 60/104,357, Oct. 15, 1995.
[51] Int. Cl.[7] .................................................. A61K 31/415
[52] U.S. Cl. .............................................................. 514/400
[58] Field of Search ...................................... 514/396, 400

[56] References Cited

U.S. PATENT DOCUMENTS 5,321,039  6/1994  Schwartz et al. ........................ 514/400
5,463,074  10/1995  Shih et al. ........................... 548/314.7

*Primary Examiner*—Raymond Henley, III
*Attorney, Agent, or Firm*—Michael J. Atkins

[57] ABSTRACT

The present invention comprises a method for treating inflammatory bowel disease (IBD) by administering to a mammal in need thereof a therapeutically effective amount of at least one histamine $H_3$-receptor agonist. It has been unexpectedly found that $H_3$-receptor agonists are effective at alleviating the effects of IBD and, therefore, are useful for treating IBD, including ulcerative colitis and Crohn's disease.

6 Claims, 3 Drawing Sheets

TREATMENT OF INFLAMMATORY BOWEL DISEASE USING HISTAMINE H$_3$-RECEPTOR AGONISTS

This application claim benefits of provisional application 60,104,357 filed Oct. 15, 1995.

BACKGROUND OF THE INVENTION

1. Field of the Invention

This invention relates to a method for treating inflammatory bowel disease by administering histamine H$_3$ receptor agonists.

2. Summary of the Related Art

Histamine (2-(4-imidazolyl)ethylamine) is found naturally in most tissues of both plants and animals. It exerts its biologic actions by combining with cellular receptors located in or on the surface membrane. There are at least three distinct types of receptors: H$_1$, H$_2$, and H$_3$. Some of the known effects of histamine are exerted on smooth muscle and cardiac muscle, on endothelial and nerve cells, and on the secretory cells of the stomach.

The histamine H$_3$ receptor is the latest receptor to have been identified (e.g., Arrang et al., Nature, 327:117 (1987) and Vander Werf et al., Trends Pharmacol. Sci., 10:159 (1989)). Stimulation of this receptor with H$_3$ receptor agonists has been employed to treat a variety of conditions such as anxiety, allergy, gastrointestinal ulcers, cardiovascular diseases, central nervous system disorders, psychiatric disorders, sexual dysfunction, and sleep disorders. The majority of the compounds synthesized for this purpose are derivatives of histamines, in other words, 2-substituted imidazoles.

More recently, H$_3$-receptor agonists have been used in the treatment of inflammation. Generally, various 2-substituted imidazoles have been synthesized to treat inflammation (e.g., Khan et al., International Publication No. WO 96/40126 and Aslanian et al., U.S. Pat. No. 5,463,074). The treatment of inflammation of the bronchi has also been specifically disclosed (Schwarz et al., U.S. Pat. No. 5,321,039).

The treatment of inflammatory bowel disease (IBD), however, has not been addressed with the use of H$_3$-receptor agonists. The principal drugs used in the treatment of (IBD) are corticosteroids and other immunosuppressive agents, as well as sulfasalazine. IBD, however, is a special type of inflammatory process whose response to anti-inflammatory compounds developed for other indications is unpredictable. Nonsteroidal anti-inflammatory drugs (NSAIDs) for instance, are potent anti-inflammatory compounds useful for treating inflammatory processes in several organs and tissues. However, many NSAIDs are ineffective in the treatment of IBD and can actually exacerbate experimental colitis in animals and activate quiescent inflammatory bowel disease in humans (e.g., Wallace et al., Gastroenterology, 102:18–27 (1992); Kaufmann et al., Annals of Internal Medicine, 107:513–516 (1987)). Therefore, it cannot be extrapolated that anti-inflammatory drugs developed to treat inflammation in other organs and tissue will also have a beneficial effect in treating IBD.

Because there are many mediators present in an inflammatory response, and inflammation in different areas have different mechanisms of action, it is difficult to predict what the correct therapy is for any specific inflammatory response. Compounds useful for treating one type of inflammatory disease or state are not necessarily useful for treating others. Therefore, the use of histamine H$_3$-receptor agonists for the treatment of IBD is a necessary and novel approach in this area of inflammation.

SUMMARY OF THE INVENTION

This invention comprises a method for the treatment of IBD by administering a therapeutically effective amount of a histamine H$_3$-receptor agonist to a mammal in need of such treatment. Evidence presented herein demonstrates that H$_3$-receptor agonists substantially reduce the effect of IBD. In a typical experiment, male rats were injected twice intraperitoneally within a twenty-four hour period with an effective amount of histamine H$_3$-receptor agonist. Sixty minutes after the second injection, the rats were injected intracolonically with an IBD inducing agent. An equal dose of agonist was injected daily for 7 days while allowing the animals to eat and drink regularly. After the 7 days of treatment, the animals were sacrificed and the last 10 cm of the colon was removed, weighed, and digitized on an image analyzer. The analyzer determined the extent of colonic damage.

The parameters measured were the weight of the colon, the extent of colonic damage, and the severity of the lesions formed. The rats injected with the histamine H$_3$-receptor agonist showed marked improvement in all three parameters. These results suggest that histamine H$_3$-receptor agonists represent a novel way to treat IBD in humans.

The foregoing merely summarizes certain aspects of the present invention and is not intended, nor should it be construed, as limiting the invention in any manner. All patents and other publications referenced herein are hereby incorporated by reference in their entirety.

DETAILED DESCRIPTION OF THE INVENTION

Figure 1:
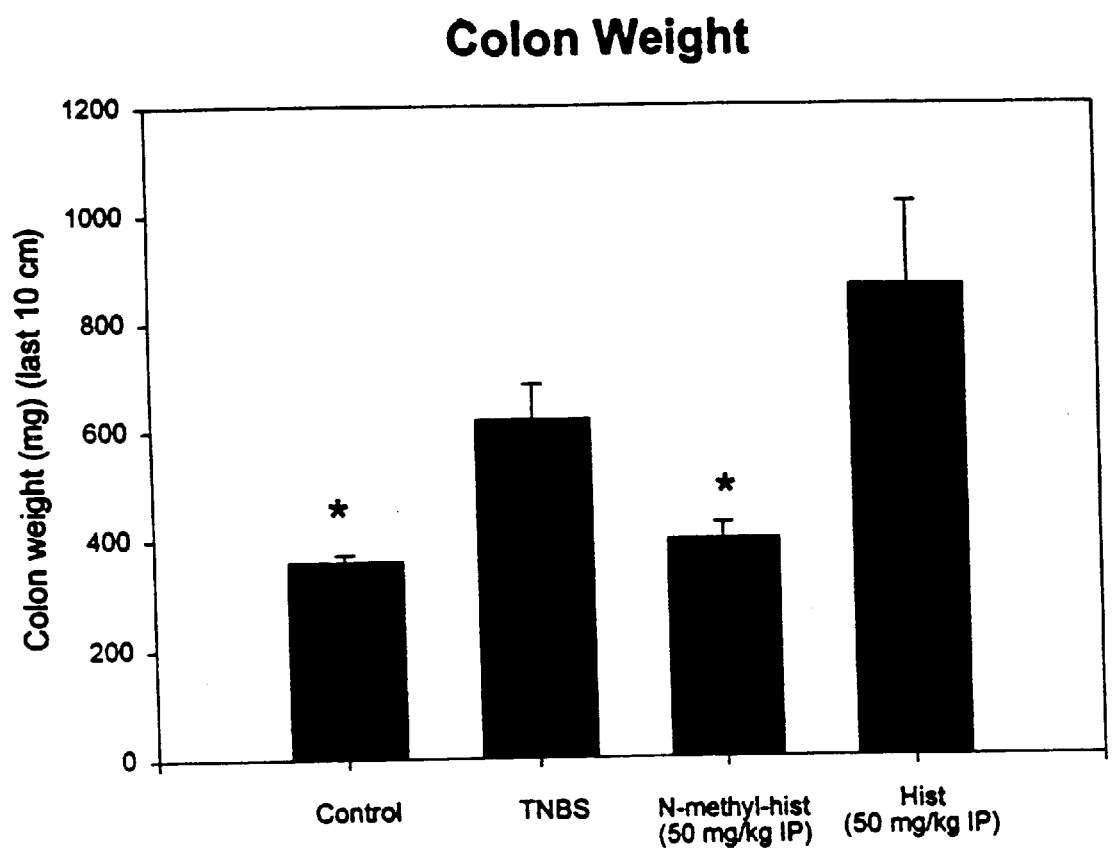
FIG. 1 displays the weight of the 10 cm colon removed from sacrificed rats treated with N-methyl-histamine and rats injected with histamine after the 7 day post-TNBS administration. The asterisks indicate $p<0.05$ compared to TNBS group (ANOVA followed by t-test).

This invention comprises a method for treating inflammatory bowel disease by administering a therapeutically effective amount of at least one histamine H$_3$-receptor agonist to a mammal (preferably human) in need of such treatment. As demonstrated herein, it has been unexpectedly found that H$_3$-receptor agonists are effective therapeutic agents for the treatment of IBD. As used herein, inflammatory bowel disease includes ulcerative colitis and Crohn's disease.

H$_3$-receptor agonists generally fall into the class of compounds consisting of 2-substituted imidazoles, particularly histamine derivatives (Patent Applications EP-A-0,214,058 and EP-A-0,338,939). Illustrative examples of histamine derivatives include, but are not limited to, N-methyl histamine (Calbiochem Coporation, Lajolla, Calif.), N,N-dimethyl histamine (Schunack, Joint Meeting of the American Chemical Society, Div. Of Med. Chem., and the American Society for pharmacology and experimental therapeutic, Boston, U.S.A., Aug. 18–22, 1985.), β-methyl histamine (Ganellin et al., *J. Med. Chem.*, 16:616 (1973) and by Schunack et al. in Frontiers in histamine research, C. R. Ganellin and J. C. Schwartz, ed. Pergamon Press, 1985, Page 39), α,β-dimethyl histamine (Patent Application EP-A-0, 338,939), β,β-dimethyl histamine (Durant et al., *J. Med. Chem.*, 19:923 (1976)), α-methyl, β-fluoro histamine, α,β-difluoro histamine, and α,β-dimethyl histamine (Patent Application EP-A-0,338,939). $H_3$-receptor agonists useful in the invention can be purchased from commercially available sources such as Calbiochem Corporation (La Jolla, Calif.) or synthesized using standard techniques (e.g., EP-A-0,338,939).

A single $H_3$-receptor agonist can by used according to the invention or a combination of such agonists may be used. Preferably, the $H_3$-receptor agonist to which the invention relates corresponds to a histamine derivative. Most preferably, the $H_3$-receptor agonist is N-methyl histamine.

The histamine $H_3$-receptor agonists may be administered orally, parenterally, by inhalation, spray, or rectally in dosage unit formulations containing conventional non-toxic pharmaceutically acceptable carriers, adjutants and vehicles. The term parenteral as used herein includes subcutaneous injections, intravenous, intramuscular, intrasternal injection, or infusion techniques. In addition, there is provided a pharmaceutical formulation comprising a histamine $H_3$-receptor agonist and a pharmaceutically acceptable carrier. One or more histamine $H_3$-receptor agonists may be present in association with one or more non-toxic pharmaceutically acceptable carriers and/or diluents and/or adjutants and if desired other active ingredients. The pharmaceutical compositions containing histamine $H_3$-receptor agonists may be in a form suitable for oral use, for example as tablets, troches, lozenges, aqueous or oily suspensions, dispersible powders or granules, emulsion, hard or soft capsules or syrups or elixirs.

Compositions intended for oral use may be prepared according to any method known to the art for the manufacture of pharmaceutical compositions and such compositions may contain one or more agents, flavoring agents, coloring agents and preserving agents in order to provide pharmaceutically elegant and palatable preparations. Tablets contain the active ingredient in admixture with nontoxic pharmaceutically acceptable excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin, or acacia, and lubricating agents, for example magnesium sterate, stearic acid, or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example calcium carbonate, calcium phosphate of kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, sodium alginate, polyvinylpyrrolidone, gum tragacanth, and gum acacia; dispersing or wetting agents may be a naturally occurring phosphatide, for example, lecithin, or condensation products of an alkylene oxide with fatty acids, for example polyoxyethylene sterate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil, or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring, and coloring agents, may also be present.

Pharmaceutical compositions may also be in the form of oil-in-water emulsions. The oily phase may be a vegetable oil, for example olive oil or arachis oil, or a mineral oil for example liquid paraffin or mixtures of these. Suitable emulsifying agents may be naturally occurring gums, for example gum acacia or gum tragacanth, naturally occurring phospatides, for example soy bean, lecithin, and esters or partial esters derived from fatty acids and hexitol, anhydrides, for example sorbitan monoleate and condensation products of the said partial esters with ethylene oxide, for example polyoxyethylene sorbitan monoleate. The emulsions may also contain sweetening and flavoring agents.

Syrups and elixirs may be formulated with sweetening agents, for example, glycol, sorbitol or sucrose. Such formulations may also contain a demulcent, a preservative and flavoring and coloring agents. The pharmaceutical compositions may be in the form of a sterile injectable aqueous or oleaginous suspensions. This suspension may be formulated according to known art using those suitable dispersing or wetting agents and suspending agents which have been mentioned above. The sterile injectable preparation may also be sterile injectable solution or suspension in a non-toxic parentally acceptable diluent or solvent, for example as a solution of 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The histamine $H_3$-receptor agonists may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Histamine $H_3$-receptor agonists may be administered parenterally in a sterile medium. The drug, depending on the vehicle and concentration used, can either be suspended or dissolved in the vehicle. Advantageously, adjutants such as local anesthetics, preservatives and buffering agents can be dissolved in the vehicle. Suitable and optimal dosages and administration regimes can be routinely determined using techniques well known to those skilled in the art.

The following examples are provided for illustrative purposes only and are not intended, nor should they be construed, as limiting the invention in any manner. Those skilled in the art will appreciate that modifications and variations of the following examples can be made without exceeding the spirit or scope of the present invention and claims.

EXAMPLES

The Assay

After 24 hours of food fasting, Male CD rats were injected intraperitoneally (IP) with N-Methyl-histamine or histamine at a dosage of 50 mg/kg (volume injected: 1 mL). Twenty-four hours later, the rats were weighed and injected as before. After 60 minutes, they were all injected intracolonically with 50 mg/kg Trinitrobenzenesulfonic acid (TNBS) dissolved in 50% ethanol (volume injected: 0.5 mL) by means of a catheter inserted 8 cm into the colon through the anus. Animals were then returned to their cages and allowed food and water ad libitum. The treatment regimen was then repeated daily for the entire duration of the experiment. Seven days after TNBS injection, the animals were sacrificed. The last 10 cm of the colon was removed, opened lengthwise, weighed, rinsed in saline and pinned out on a flat surface. The image of the colon was then digitized on an Olympus CUE3 image analyzer (Olimpus Corp., Marietta, Ga.).

Colon Weight

The wet weight of the last 10 cm of the colon was recorded immediately prior to digitization of the sample. Results for N-Methyl-histamine and histamine are shown in FIG. 1. Data is expressed as colon weight in mg of the last 10 cm of colon. The colon weight of the animal treated with N-Methyl-histamine was less than half of the animals injected with histamine.

Extent of Damage

Figure 2:
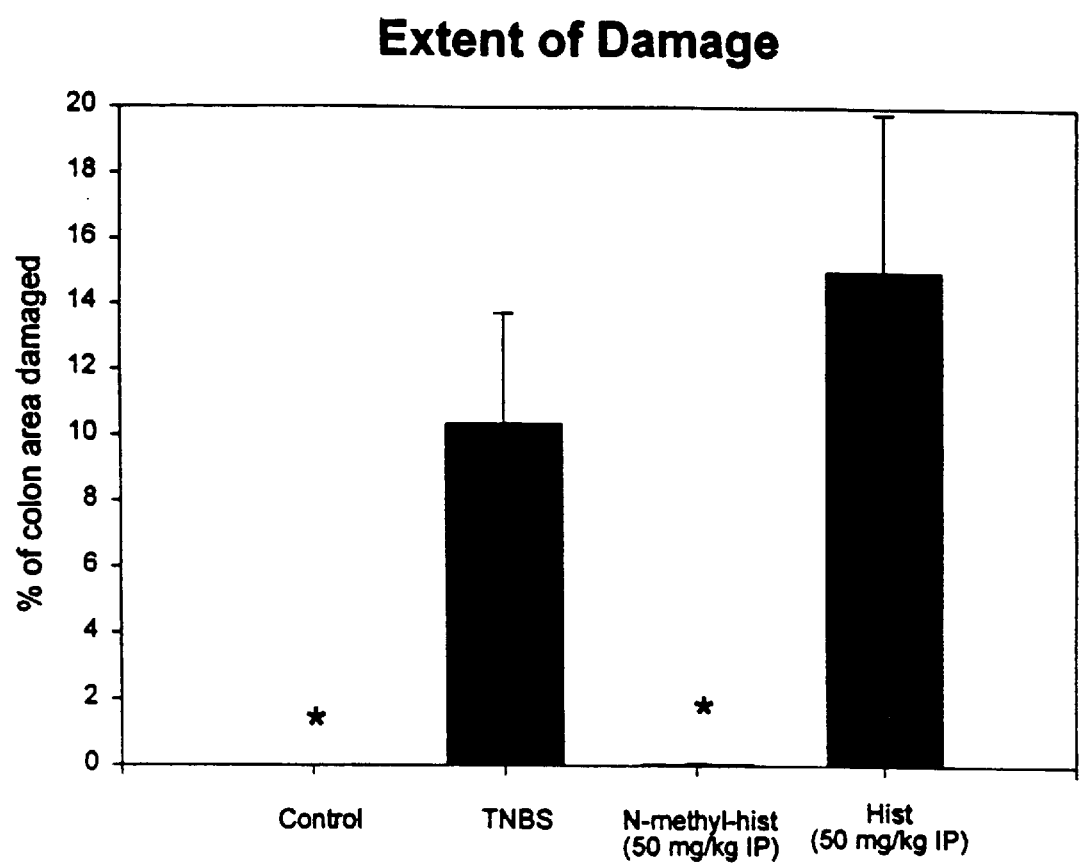
FIG. 2 displays the percentage of colon area damaged from rats treated with N-methyl-histamine and rats injected with histamine after the 7 day post-TNBS administration. The asterisks indicate $p<0.05$ compared to TNBS group (ANOVA followed by t-test).

The extent of colonic damage was determined by means of the computerized image analyzer mentioned above. The image of the colon was retrieved and areas of abnormal color were automatically identified and measured by the computer. The total area of the sample was also determined. Results are shown in FIG. 2. Data is expressed as percentage of the total area damaged in the last 10 cm of the colon. The percentage of colon area damaged in the N-methyl-histamine treated animals was less than 1%.

Severity Score

Figure 3:
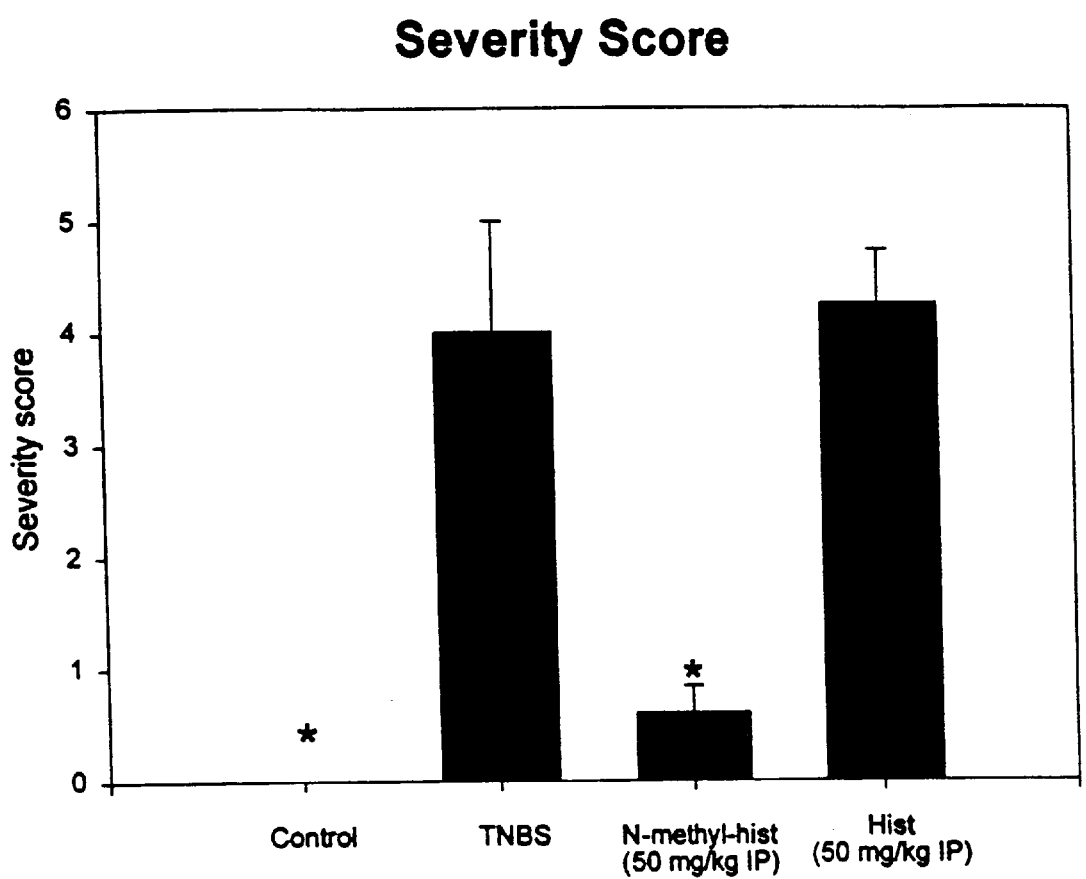
FIG. 3 displays the severity score of rats treated with N-Methyl-histamine and rats injected with histamine after 7 day post-TNBS administration. The asterisks indicate $p<0.05$ compared to TNBS group (ANOVA followed by t-test). The severity score was calculated according to Gastorenetrology, 96:795–803 (1989).

The severity of the lesions was scored according to the score published by Morris et al. for TNBS lesions (*Gastroenterology*, 96:795–803, (1989)). Results are shown in FIG. 3. The severity score for animals treated with N-methyl-histamine were half the value for those animals injected with histamine.

The improved condition of rats treated with the histamine $H_3$-receptor agonist N-methyl-histamine is evident from the results of all three parameters. This suggests a novel approach for the treatment of IBD.

What is claimed is:

1. A method of treating inflammatory bowel diseases comprising administering a therapeutically effective amount of at least one histamine $H_3$-receptor agonist to a mammal in need of such treatment.

2. A method according to claim 1 wherein the mammal is a human.

3. A method according to claim 1 wherein the histamine $H_3$-receptor agonist is a histamine derivative.

4. A method according to claim 3 wherein the histamine derivative is N-methyl-histamine.

5. A method according to claim 1 wherein the inflammatory bowel disease is ulcerative colitis.

6. A method according to claim 1 wherein the inflammatory bowel disease is Crohn's disease.

* * * * *

UNITED STATES PATENT AND TRADEMARK OFFICE
CERTIFICATE OF CORRECTION

PATENT NO. : 6,028,095
DATED : February 22, 2000
INVENTOR(S) : Antonio Guglietta It is certified that error appears in the above-identified patent and that said Letters Patent is hereby corrected as shown below:

Title page, item [60], Related U.S. Application Data, "Provisional application No. 60/104,357, Oct. 15, 1995" should read "Provisional application No. 60/104,357, Oct. 15, 1998".

Column 1, line 6, "October 15, 1995", should read "October 15, 1998".

Signed and Sealed this

Fourteenth Day of November, 2000

*Attest:*

Q. TODD DICKINSON

*Attesting Officer*   *Director of Patents and Trademarks*